United States Patent [19]

Cordi et al.

[11] Patent Number: 5,061,721

[45] Date of Patent: Oct. 29, 1991

[54] COMPOSITION CONTAINING D-CYCLOSERINE AND D-ALANINE FOR MEMORY AND LEARNING ENHANCEMENT OR TREATMENT OF A COGNITIVE OR PSYCHOTIC DISORDER

[75] Inventors: Alex A. Cordi, St. Louis, Mo.; Michel R. Jans, Brussels, Belgium

[73] Assignee: G. D. Searle & Co., Chicago, Ill.

[21] Appl. No.: 473,241

[22] Filed: Feb. 6, 1990

Related U.S. Application Data

[63] Continuation-in-part of Ser. No. 324,279, Mar. 15, 1989, abandoned.

[51] Int. Cl.$^5$ .................. A61K 31/42; A61K 31/195
[52] U.S. Cl. ...................................... 514/376; 514/561
[58] Field of Search ................................ 514/376, 561

[56] References Cited

U.S. PATENT DOCUMENTS 3,428,730  2/1969  Umezawa et al. .................. 424/114
4,031,231  6/1977  Kohar ................................ 514/561
4,904,681  2/1990  Cardi et al. ........................ 514/380

OTHER PUBLICATIONS

S. I. Deutsch et al., *Clinical Neuropharmacology*, 12(1), 1–13, (1989).
*The Merck Index*, Monograph No. 2747, 10th Ed., Merck & Co., p. 395 (1983).
Goodman & Gilman, *The Pharmacological Basis of Therapeutics*, 7th Ed., MacMillan, New York, p. 1209 (1985).
Drug Evaluation, Chapter 75, *American Medical Association*, Chicago (1986).
G. K. McEvoy et al., *American Hospital Formulary Service: Drug Information*, 8:16, American Society of Hospital Pharmacists, Bethesda, MD (1986).
W. B. Sutton et al., *Antibiot. Chemotherapy*, 5, 582–584 (1955).
M. Borgia et al., *Curr. Therap. Res.*, 31, 2, 265–271 (1982).
J. W. Moulder et al., *J. Bacteriol.*, 85, 707–711 (1962).
U. Roze et al., *Mol. Pharmacol.*, 2, 92–94 (1966).

*Primary Examiner*—Stanley J. Friedman
*Attorney, Agent, or Firm*—J. Timothy Keane; Paul D. Matukaitis

[57] ABSTRACT

A composition is described for use in memory and learning enhancement or for treatment of a cognitive disorder or a psychotic disorder. This composition contains the compound D-cycloserine and D-alanine and provides reduced adverse side effects typically associated with chronic D-cycloserine use.

17 Claims, 2 Drawing Sheets

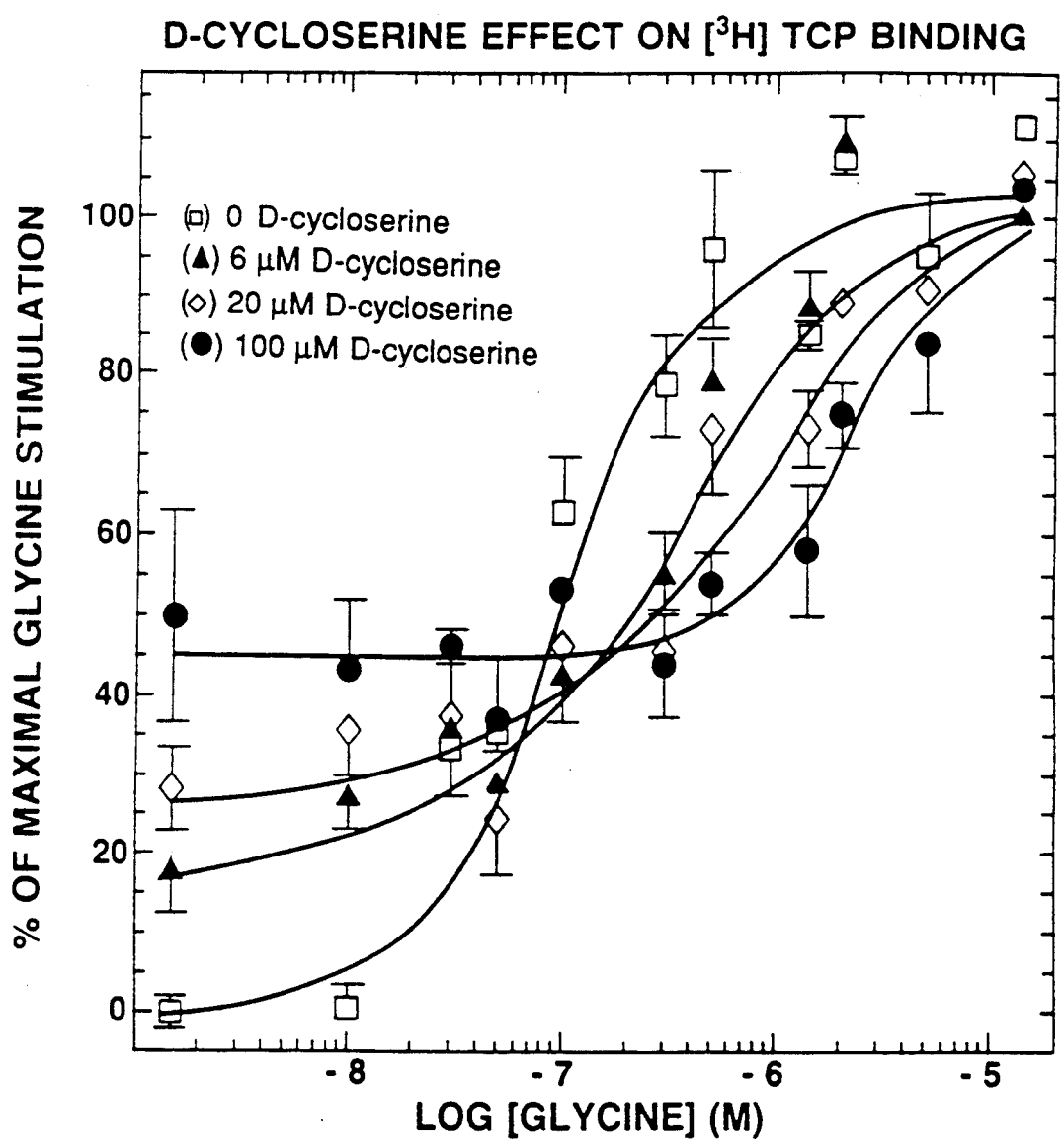

COMPOSITION CONTAINING D-CYCLOSERINE AND D-ALANINE FOR MEMORY AND LEARNING ENHANCEMENT OR TREATMENT OF A COGNITIVE OR PSYCHOTIC DISORDER

CROSS REFERENCE TO RELATED APPLICATION

This application is a continuation-in-part of U.S. application Ser. No. 07/324,279 filed Mar. 15, 1989, now abandoned.

FIELD OF THE INVENTION

This invention is in the field of clinical neurology and relates specifically to compounds, formulations and methods for memory enhancement and for treatment of cognitive and psychotic disorders.

BACKGROUND OF THE INVENTION

There are many memory-related conditions for which therapeutic treatments are under investigation, such as methods to enhance memory or to treat memory dysfunction. For example, memory dysfunction is linked to the aging process, as well as to neurodegenerative diseases such as Alzheimer's disease. Also, memory impairment can follow head trauma or multi-infarct dementia. Many compounds and treatments have been investigated which can enhance cognitive processes, that is, which can improve memory and retention.

For example, the compound D-cycloserine has been discovered recently to provide improvements in cognitive function and to be useful in treatment of cognitive dysfunction, as described in U.S. Pat. application Ser. No. 07/127,121 filed Dec. 1, 1987, now U.S. Pat. No. 4,904,681 and application PCT/US88/04244 filed Dec. 1, 1988.

There are many psychotic states for which therapeutic treatments are under investigation. Drugs which are currently available on the market are thought to act as antagonists at the dopaminergic receptors located in the Central Nervous System (CNS), examples of such drugs being haloperidol and chlorpromazine. These drugs typically induce long lasting and sometimes irreversible side-effects, such as tardive dyskinesia. Thus, the search for improvements in therapy for psychotic disorders has been directed to use of drugs with a different mode of action.

Phencyclidine [1-(-phenylcyclohexyl)piperidine; PCP] is a known general anesthetic and is in use as an animal tranquilizer. PCP is a potent psychotomimetic agent used frequently as a "street" drug. Widespread abuse of PCP has led to increased incidence of PCP-induced psychoses [C. V. Showalter et al, *Amer. J Psychiat.*, 134, 1234 (1977)]. PCP abusers experience an apparent sensory isolation accompanied by a feeling of depersonalization which can be terrifying to the person. These subjective changes make PCP an appropriate drug model for study of schizophrenia. The most impressive evidence that PCP psychosis resembles schizophrenia is the fact that drug users have been mistaken by experienced psychiatrists for schizophrenics before obtaining the history of drug use [S. H. Snyder, *Nature*, 355–356 (1980)].

PCP has been reported to modulate allosterically the NMDA receptor [P. Loo et al, *Eur. J. Pharmacol.*, 467–468 (1986)] and it has been speculated that the psychotomimetic activity of PCP is related to its antagonism of NMDA transmission [C. A. Tamminga et al, *Synapse*, 1, 497–504 (1987)]. Facilitation of NMDA transmission by action at the glycine modulatory site may antagonize the effect of an endogenous PCP-like ligand [R. Quirion et al, *Peptides*, 5, 967–973 (1984)]. Also it has been postulated that glutamatergic action at the glycine-modulated NMDA receptor may be a route to treatment of schizophrenic [S. I. Deutch et al, *Clin. Neuropharm.*, 12, 1, 1–13 (1989)].

D-cycloserine has long been known as a bacteriostatic agent [see *The Merck Index*, Monograph No. 2747, 10th Edn., Merck & Co., p.395 (1983)]. Its mechanism of action is believed to involve inhibition of cell wall synthesis in susceptible organisms by competing with D-alanine for incorporation into the bacterial cell wall. Also, it is known that the in vitro antibacterial activity of D-cycloserine may be inhibited with D-alanine [Goodman & Gilman, *The Pharmacologic Basis of Therapeutics*, 7th Edn., MacMillan, N.Y., p. 1209 (1985)].

The compound D-cycloserine, in its D- and L-isomer forms, has also been evaluated for CNS effects in animals [O. Mayer et al, *Arzneim. Forsch.*, 21(2), 298–303 (1971)]. These cycloserine isomers have also been evaluated for psychological and physiological effects in human subjects. For example, D-cycloserine when administered at 500 mg/day doses to healthy human subjects, appeared to stimulate slight sociability, but with depressed mental alertness [M. Vojtechovsky, *Act. Nerv. Super.*, 7(3) 269 (1965)]. Also, D-cyloserine has been administered at 1000 to 1500 mg/day to healthy volunteers whose blood levels showed increased levels of monoamine oxidase enzyme activity [V. Vitek et al, *Psychopharmacologia*, 7(3), 203–219 (1965)].

D-cycloserine has been investigated as a therapeutic agent for mental disorders in clinical trials, wherein D-cycloserine was administered to mentally disturbed patients at doses of 500 mg. per day [G. E. Crane, *Compr. Psychiat.*, 2, 51–53 (1961)]. In such clinical trials, improvements in depression, insomnia, anexoria or tension were found for some patients, while patients suffering from severe neurosis or psychosis responded poorly to such medication. Moreover, D-cycloserine has been used to exacerbate the symptoms of schizophrenia in an attempt to cure the ailment by symptom provocation [J. Simeon et al, *Compr. Psychiat.*, 11, 80–88, (1970)]. It appears that D-cycloserine, at the dose levels used in these studies, is acting as an antagonist at the glycine site of the NMDA-PCP receptor complex mimicking the action of PCP by inducing psychosis.

D-cycloserine has been sold commercially for treatment against Mycobacterium tuberculosis. When used at tuberculostatic doses, D-cycloserine is accompanied by many adverse side effects. The most frequent adverse side effects known involve the nervous system. In fact, the limiting factor in use of cycloserine is its CNS toxicity, including both neurologic and psychic disturbances [*Drug Evaluation*, Chapter 75, American Medical Association, Chicago (1986)]. Patients receiving D-cycloserine have been noted to suffer from drowsiness, dizziness, headache, lethargy, depression, tremor, dysarthria, hyperreflexia, paresthesia, nervousness, anxiety, vertigo, confusion and disorientation with loss of memory, paresis, major and minor clonic seizures, convulsions and coma [G. K. McEvoy et al, *American Hospital Formulary Service: Drug Information*, 8:16, American Society of Hospital Pharmacists, Bethesda, Md. (1986)].

Other side effects have also been associated with treatments using D-cycloserine. In chronic administration of tuberculostatic doses to patients in clinical trials, D-cycloserine has been observed to produce episodes of diarrhea and oral mucositis. Diarrhea episodes are believed to be linked to depletion of natural intestinal flora by D-cycloserine interference with flora cellular production. Several attempts have been made to reverse this flora depletion effect associated with D-cycloserine treatments. For example, the antibacterial effect of D-cycloserine on Mycobacterium paratuberculosis has been reversed by mycobactin [W. B. Sutton et al, *Antibiot. Chemotherapy*, 5, 582-584 (1955)]. Patients under treatment with tuberculostatic doses of D-cycloserine, and suffering from diarrhea, have been given preparations of *Streptococcus faecium* which reduced significantly the episodes of diarrhea [M. Borgia et al, *Curr. Therap. Res.*, 31, 2, 265-271 (1982)]. It is also a well-known remedy to use certain aged, fermented cheeses, such as Camembert or Maroilles cheese, to restore flora depleted by antibiotic treatment.

The growth-inhibiting effect of D-cycloserine on bacteria has been shown to be competitively reversed by D-alanine, a compound noted to be a structural analogue of D-cycloserine [J. W. Moulder et al, *J. Bacteriol.*, 85, 707-711 (1962)]. It has been found that D-cycloserine, as a competitive inhibitor of alanine racemase, is bound to the alanine racemase enzyme 100 times more effectively than the natural substrate D-alanine [U. Roze et al, *Mol. Pharmacol.*, 2, 92-94 (1966)].

Other interactions between D-cycloserine and alanine-type compounds are known. For example, U.S. Pat. No. 4,031,231 describes antibacterial compositions containing 3-fluoro-D-alanine-type compounds, such as 3-fluoro-D-alanine and its deutero analogues, in combination with a 3-fluoro-D-alanine autoantagonist-inhibitor, such as D-cycloserine. These compositions are described as having synergistic antibacterial action.

BRIEF DESCRIPTION OF FIGURES

FIG. 2 is a graph showing concentration of glycine influence on maximal glycine stimulation of TCP binding in the presence of various concentrations of D-cycloserine.

DESCRIPTION OF THE INVENTION

Figure 1:
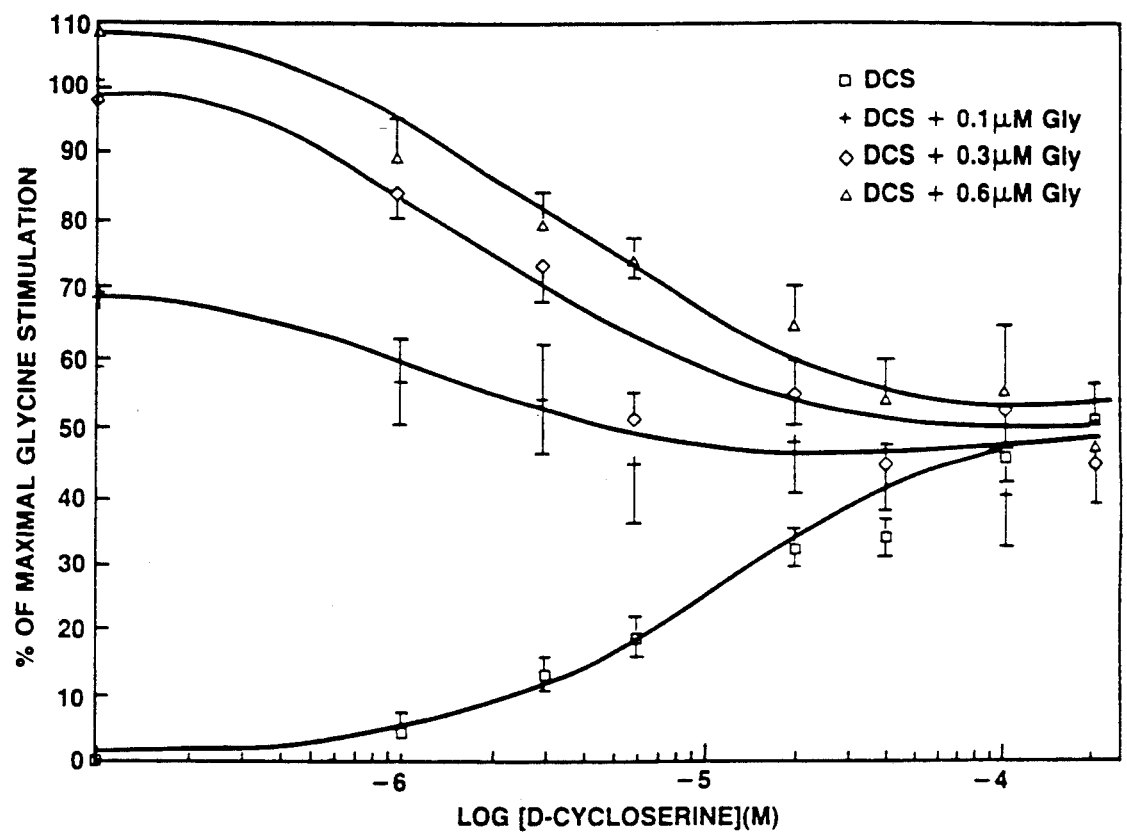
FIG. 1 is a graph showing concentration of D-cycloserine influence on maximal glycine stimulation of TCP binding in the presence of various concentrations of glycine.

A therapeutic method for improvement of cognitive function or treatment of a cognitive dysfunction or a psychotic disorder is achieved by treatment of a subject, when such therapy is indicated, with a combination therapy of a therapeutically-effective amount of a cycloserine-type compound and a therapeutically-effective amount of D-alanine. The phrase "combination therapy", as used herein, is intended to embrace administration of the cycloserine and D-alanine components in a sequential manner or to embrace co-administration of these two components in a simultaneous manner. Co-administration of these two components for cognitive-function improvement or cognitive-dysfunction treatment or antipsychotic treatment, may be accomplished with a pharmaceutical composition having as active components a therapeutically-effective amount of a cycloserine-type compound and a therapeutically-effective amount of D-alanine. Preferably this composition will contain one or more pharmaceutically-acceptable excipients. More preferred is a pharmaceutical composition consisting essentially of a therapeutically-effective amount of a cycloserine compound and a therapeutically-effective amount of D-alanine. A therapeutically-effective amount of D-alanine is defined as a side-effect suppressing amount of D-alanine. Examples of adverse side-effects which can be prevented or reduced by D-alanine administration are gastro-intestinal related distresses such as diarrhea and destruction of the intestinal flora.

A preferred type of cycloserine compound is D-cycloserine. The pharmaceutical composition should contain D-cycloserine and D-alanine in a therapeutically-effective ratio.

The phrase "therapeutically-effective ratio" embraces a range of relative amounts of D-alanine and D-cycloserine which will be effective to improve cognitive dysfunction or to treat psychosis, while at the same time being effective to reduce adverse side effects associated with use of D-cycloserine alone. Improvement in cognitive function means generally improvement in memory or learning ability. Treatment of cognitive dysfunction includes treatment of neurodegenerative diseases such as Alzheimer's disease, age-associated memory impairment or a learning deficit. It is believed that a psychotic disorder is linked to an increased concentration of an endogenous ligand acting at the PCP site of the NMDA-PCP receptor complex. This endogenous ligand is believed to be PCP-like in character in that interaction of the ligand with the NMDA-PCP receptor complex results in inhibition of the opening of the ion channel triggered by NMDA. A Glycine B agonist compound of the invention, by potentiating NMDA transmission, will thus antagonize the effect of the endogenous ligand. Inasmuch as the endogenous ligand is responsible for psychotic disorders, such as schizophrenia, the blocking of such ligand action should result in reduction of psychotic behavior. In particular, it is believed that the compounds of the invention will be useful in the treatment of acute or chronic PCP-induced psychosis.

A therapeutically-effective ratio of D-alanine to D-cycloserine would be in a range from about 1-to-1 to about 100-to-1.

D-cycloserine is 4-amino-3-isoxazolidone having the structural formula

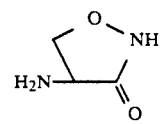

This compound exists in the L- and D-isomeric forms, of which the compound D-cycloserine is more highly preferred.

Also embraced by this invention are the tautomeric forms of the foregoing cycloserine compounds as represented by

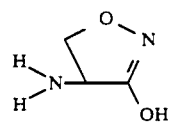

Included within the family of compounds of this invention are the isomeric forms of the described compounds including diastereoisomers, and the pharmaceutically-acceptable salts thereof. The term "pharmaceutically-acceptable salts" embraces salts commonly used to form alkali metal salts and to form addition salts of free acids or free bases. Since the cycloserine compounds contain basic nitrogen atoms, such salts are typically acid addition salts or quaternary salts. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. All of these salts may be prepared by conventional means by reacting, for example, the appropriate acid or base with the corresponding cycloserine compound.

Cycloserine compounds for use in the invention may be synthesized by methods described in the literature. For example, syntheses of N-acyl derivatives and Schiff-base derivatives of D-cycloserine are described by N. P. Jensen et al, *J. Med. Chem.*, 23 6-8 (1980). Syntheses of N,N'-diacyl derivatives of cycloserine are described by J. C. Howard, *J. Org. Chem.*, 46, 1720-1723 (1981). . Syntheses of alkyl derivatives of cycloserine are described by C. H. Stammer, *J. Med. Chem.*, 13(6), 1013 (1970). Syntheses L- and D-isomers of cycloserine, as well as analogues thereof, are described by Pl. A. Plattner et al, *Helv. Chim. Acta.*, 40 1531 (1957). There are many commercial sources of D-alanine, as well as many published methods for making D-alanine.

BIOLOGICAL EVALUATION

Glycine Binding Assay Procedure

Synaptic plasma membranes (SPM) were prepared from rat forebrain and stored as previously described [J. B. Monahan and J. Michel, *J. Neurochem.*, 48, 1699-1708 (1987)]. Frozen membranes were thawed and diluted 1:20 with 0.04% triton X-100 in 50 mM tris/acetate (pH 7.4). Following incubation at 37° C. for 30 min., the SPM were collected by centrifugation at 95,000 X g for 15 min. The pellet was resuspended in 50 mM tris/acetate (pH 7.4, triton-free) and hand-homogenized five times. The membranes were again centrifuged as above. The pellet was washed two additional times with 50 mM tris/acetate (without homogenization) and centrifuged. The final pellet was resuspended with homogenization in 50 mM tris/acetate.

In the general receptor binding assay procedure, 10 nM [$^3$H]glycine was added to the appropriate concentration of the test compounds and the assay initiated by the addition of 0.2-0.4 mg of ice cold SPM. The assay, which was done in 1.5 ml centrifuge tubes, was adjusted to a total volume of 1.0 ml with all additions being made in 50 mM tris/acetate, pH 7.4 at 4° C. After a 10 minute incubation at 2° C., the samples were centrifuged for 15 min. at 12,000 g (4° C.) in a Beckman Microfuge 12. The supernatant was aspirated and the tube tip containing the pelleted membranes cut off and agitated in 0.5 ml of Beckman BTS-450 tissue solubilizer for a minimum of 6 hours at room temperature. Beckman MP scintillation cocktail (5 ml) containing 7 ml/liter acetic acid was then added and the samples counted on a Beckman LS 5800 liquid scintillation counter with automatic corrections for quenching and counting efficiency. Nonspecific binding was defined as the residual binding in the presence of 0.1 mM glycine and usually amounted to 25-35% of the total binding The binding of [$^3$H]glycine to the SPM was analyzed using Scatchard and Hill transformations and the $K_i$ for other compounds was determined using logit-log analysis. Calculations and regression analysis were performed using templates developed for Lotus 123 as previously described.

| Result | $K_i$ ($\mu$M) |
|---|---|
| Glycine | 0.18 |
| D-cycloserine | 1.92 |
| L-cycloserine | >100 |

TCP Modulation Assay

[$^3$H]TCP binding was performed using Triton X-100 washed synaptic plasma membranes (SPM) prepared from rat forebrain (30-45 day old, male Sprague-Dawley; Sasco, St. Charles, Mo.) as described previously [J. W. Thomas, W. F. Hood, J. B. Monahan, P. C. Contreras and T. L. O'Donohue, *Brain Res.*, 442, 396-398 (1988)]. The assay was initiated by the addition of SPM (0.15-0.25 mg) to an incubation containing 2.0 nM [$^3$H]TCP (47.1 Ci/mmole; New England Nuclear, Boston, Mass.) and various concentrations of the appropriate test compound in a total volume of 0.5 ml (all additions were made in 5 mM Tris/HCl buffer, pH 7.4) and continued for 60 min at 25° C. The samples were then filtered though glass fiber filters (Schleicher and Schuell #32) which were pretreated with 0.05% (v/v) polyethylenimine. The filters were washed and the radioactivity quantitated by liquid scintillation spectrometry. Stimulation of [$^3$H]TCP binding was measured as an increase in basal specific binding (basal binding=2583 ±381 DPM and this value increased to a maximum of 4712±779 DPM in the presence of 0.6 $\mu$M glycine) with nonspecific binding as the residual binding in the presence of 60 $\mu$M PCP (562±30 DPM). The $K_d$ for [$^3$H]TCP under basal conditions was 44 nM. The EC$_{50}$ values for the stimulation of [$^3$H]TCP binding were determined using a four parameter logistic regression analysis.

D-Cycloserine stimulates basal [$^3$H]TCP binding in a dose dependent manner with an EC$_{50}$=19.7 $\mu$M. Previous data show that D-cycloserine interacts with the NMDA-associated [$^3$H]glycine recognition site ($K_i$=2.33±0.29 $\mu$M). No affinity for the NMDA recognition site, however, was detected as evidenced by the lack of displacement of NMDA-specific L-[$^3$H]glutamate binding ($K_i$>100 $\mu$M). This finding indicates that D-cycloserine enhances [$^3$H]TCP binding through its interaction with the NMDA receptor-associated glycine recognition site (herein defined as the "Glycine B receptor"). The maximal stimulation produced by D-cycloserine, however, was significantly less than that produced by both glycine and D-serine.

This apparent lower efficacy indicates the potential partial agonist character of D-cycloserine which was confirmed by the following experiment. As shown in FIG. 1, in the absence of exogenously added glycine, D-cycloserine has agonist properties and stimulates [H]TCP binding to a maximum of 40-50% of the stimulation induced by glycine alone. However, in the presence of various concentrations of glycine (0.1-0.6 μM), D-cycloserine has an apparent antagonist character and reduces the maximal level of glycine stimulation. These data provide a family of D-cycloserine dose-response curves (generated in the presence of several fixed concentrations of glycine) which asymptotically approach 40-50% of the maximal stimulation induced by glycine alone, a pattern characteristic of compounds with partial agonist properties as is known with different compounds acting on other receptors.

Further confirmation of the partial agonist character of D-cycloserine was demonstrated in experiments wherein a glycine dose-response analysis was performed in the presence of several fixed concentrations of D-cycloserine (0-100 μM). As shown in FIG. 2, D-cycloserine potentiated the glycine stimulation of [$^3$H]TCP binding at glycine concentrations below 0.1 μM, while at higher glycine concentrations (0.1-15 μM) D-cycloserine produced a rightward shift in the dose-response curve. These results are again consistent with partial agonist characteristics.

The functional analysis of D-cycloserine described herein is the first report of a compound interacting at this glycine modulatory site exhibiting partial agonist characteristics. These results along with the favorable brain bioavailability of the compound and evidence for involvement of the NMDA receptor in learning and memory potentially make D-cycloserine a valuable tool to probe NMDA receptor function. More importantly, Glycine B partial agonists would be expected to provide therapeutic benefits in treatment of psychosis, cognitive dysfunctions, such as Alzheimer's Disease, age-associated memory impairment, multi-infarct dementia, mixed organic brain syndrome metabolic encephalopathies of various origins, alcoholic dementia and various learning disorders. In particular, the Glycine B partial agonist compounds would be useful in treatment of schizophrenia, Alzheimer's Disease, age-associated memory impairment and learning deficit, in human subjects suffering from such disorders, as well as for use in improvement of memory and learning ability in healthy individuals.

PASSIVE AVOIDANCE ASSAY METHODS

Subjects: Male Long-Evans rats weighing about 200 g (Sasco) were used. They were housed two per cage with ad lib food and water for the duration of the experiment.

Apparatus: The apparatus consisted of a plexiglass box (32×26×20 cm) with a lid with a floor of metal rods spaced 1.8 cm apart. The box was divided into two chambers, one painted black and the other gray. Two doors (12 cm high) were cut into the front of the box allowing access into each chamber.

A Y-shaped plexiglas runway was attached to the front of the box. The stem of the Y was 16 cm long and unpainted. The arms of the Y (14 cm long each) led to the two doors and each was painted the color of the chamber to which it led. The stem of the Y extended over the edge of the table on which the apparatus was placed, so that it was approximately 75 cm above the floor. The metal floor of the box was wired to a Lafayette shock generator so that a 0.5 mAmp shock could be delivered.

Procedure: On the first rest day, each rat was placed on the runway and allowed to enter one of the chambers. The door to this chamber was then closed, and the rat was then allowed to enter the other chamber. On the second test day, some of the rats were given i.p. injections of either D-cycloserine dissolved in 0.9% saline, or saline alone. Sixty minutes later, each rat was again allowed to enter one chamber, where it received a footshock for 2 seconds. If the rat did not previously receive an injection, it was injected with either D-cycloserine or saline ten seconds after the footshock. On the third test day, the rat is again placed on the runway and allowed to enter a chamber. On days two and three, each rat's latency to enter a chamber, and which chamber it entered, are recorded.

Effects of D-cycloserine (10 mg/kg i.p.) on passive avoidance learning latency (secs.) to enter box 24 hours after shock are shown in Table I.

TABLE I

|  | Time of Drug Treatment | |
| --- | --- | --- |
|  | Before Shock | After Shock |
| Saline | 8.9 ± 1.5 | 14.8 ± 3.1 |
|  | (n = 6) | (n = 5) |
| D-cycloserine | 16.6 ± 3.0 | 22.8 ± 2.4 |
|  | (n = 6) | (n = 6) |

In this animal model for demonstrating memory enhancement, the delay in time for the rat to enter the chamber (the "latency period") is a measure of the rat's memory of the previous experience in receiving a foot shock. The longer is the latency period, the better is the memory enhancing effect of the tested compound. Those animal experiments show that D-cycloserine acting as a glycine ligand has memory-enhancing effect which is characterized in this model by an increased latency for the animal to enter the compartment.

The dose-effect relationship of D-cycloserine, as well as the effect of this compound when administered just before the information retrieval trial, were also studied, as reported in Table II.

TABLE II

| Dose of DCS (mg/kg i.p.) | % of Saline Control Latency in Passive Avoidance | | Administration pre-retrieval |
| --- | --- | --- | --- |
|  | pre-shock (%) | post-shock (%) |  |
| Saline | 100 | 100 | 100 |
| 0.3 | 152* | 160* | 105 |
| 3 | 245* | 215* | 153* |
| 10 | 138* | 153* | 180* |
| 20 |  |  | 100 |

*Statistically different from control (P<0.05, t-test)

The effect of co-administration of D-cycloserine and D-alanine to rats was investigated following the methodology described for Table II. Results are shown in Table III.

TABLE III

| Latency in Seconds in Passive Avoidance | | |
| --- | --- | --- |
| Compound | Dose (mg/kg I.G.) | Latency (sec.) |
| Saline |  | 11.9 |
| D-alanine | 534 | 10.9 |
| D-cycloserine | 60 | 17.3* |
| D-alanine + D-cycloserine | 534 + 60 | 17.4* |

*Statistically different from control (P<0.05, t-test)

These results in Table III show that the memory enhancement effect of D-cycloserine is not altered when D-cycloserine is co-administered with D-alanine.

Rewarded Alternation of Rats in a T-maze

Rats were trained on a place learning task in a T-maze following i.p. administration of D-cycloserine (3 mg/kg) or saline. Both groups learned the task in about 20 trials. Learning is defined as making 9 correct out of 10 consecutive choices. On the following day, the food reward was placed in the other arm of the maze (reversal). The saline-treated rats required about 32 trials to learn the reversal, while the D-cycloserine rats learned the reversal in about 20 trials. These data confirm in this behavioral paradigm that D-cycloserine has a facilitating effect on processes of learning and memory.

Intact hippocampal structure is necessary for the brain to process information and store it in memory. The phenomenon of "long term potentiation" (LTP) seems to be the mechanism by which this process occurs. The leading role of the N-methyl-D-aspartate ("NMDA") receptor, a sub-type of excitatory amino acid receptor, in LTP has been firmly established by electrophysiological studies. NMDA antagonists such as 2-amino-7-phosphonoheptanoic acid (APH) inhibit the establishment or propagation of LTP.

Recently, it has been demonstrated in neurophysiological studies that glycine potentiates the response to activation of NMDA receptors in cultured brain neurons. This is a strychnine-insensitive action and it is postulated to result from activation of a supraspinal glycine receptor (herein defined as the Glycine B receptor) which modulates the opening of the $Na^+$-$Ca^{++}$ channel triggered by NMDA activation. For example, milacemide, as a glycine prodrug, increases the whole brain content of glycine by 30%. By the mechanism explained above, this increase of glycine can lead to a facilitation of NMDA transmission and improved memory and learning ability.

Data presented in Table II demonstrate that the dose-effect relationship of D-cycloserine is characterized by a bell-shaped curve. The unusual relationship is believed to be associated with the partial agonist character of D-cycloserine. It is apparent, therefore, that maximum efficacy will be achieved within a defined range and that higher doses e.g., greater than 500 mg per dose in human subjects, would be expected to result in reduced efficacy.

The acidic amino acids, aspartic and glutamic acid, have been found to possess both excitatory and excitotoxic properties [J. W. Olney, Science, 164, 719–721 (1969); J. W. Olney et al., Exp. Brain Res., 14, 61–76 (1971)]. Indeed, neurons which have excitatory amino acid receptors on their dendritic or somal surfaces undergo acute excitotoxic degeneration when these receptors are excessively activated by glutamic acid.

Glycine agonists which have a potentiating effect on the NMDA transmission would be expected to increase the glutamic acid excitotoxicity. A Glycine B partial agonist achieves beneficial excitatory effects without the detrimental excitotoxic side effect Most glycine ligands are very polar molecules and hardly cross the blood brain barrier. Because of the difficulty in crossing the blood brain barrier, such ligands are not bioavailable at concentrations effective to be therapeutically beneficial. It is known that D-cycloserine easily passes the blood brain barrier [Goodman and Gilman, The Pharmacologic Basis of Therapeutics, Ch., 53, 1210–1211 (1980)]. It was surprising and unexpected that D-cycloserine was found to have such a good affinity for the strychnine-insensitive glycine receptor as shown by the binding data above. Glycine agonists are believed to facilitate NMDA transmission and, therefore, to have a positive effect on LTP. The improvement in LTP is postulated to be linked to memory enhancement. Such glycine agonists are also believed to have potential for reversing the symptoms of schizophrenia and, in particular, to reverse the symptoms induced by acute or chronic PCP intoxication.

Sequential or co-administration of a cycloserine compound and D-alanine may be achieved by any technique capable of introducing the combination of compounds into the gastrointestinal system.

Such combinations indicated for prophylactic therapy will preferably be administered in a ratio range from about 1:1 to about 100:1 of D-alanine to the cycloserine compound. Preferably, the ratio of D-alanine to D-cycloserine will be in a range from about 10:1 to about 100:1. In general, such combinations may be administered based upon the dose of D-cycloserine effective to enhance memory or treat cognitive dysfunction. Such effective amount of D-cycloserine will generally be in a daily dose in a range from about 0.01 mg to about 10 mg per kilogram of body weight per day. A more preferred dosage will be a range from about 0.01 mg to about 5 mg per kilogram of body weight. Most preferred is a dosage in a range from about 0.05 to about 2.5 mg per kilogram of body weight per day. A suitable dose can be administered in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compounds are usually administered in a pharmaceutically-acceptable formulation. Such formulations may comprise effective amounts of each active compound together with one or more pharmaceutically-acceptable carriers or diluents. Other therapeutic agents may also be present in the formulation. A pharmaceutically-acceptable carrier or diluent provides an appropriate vehicle for delivery of the active compounds without introducing undesirable side effects. Delivery of the active compounds in such formulations may be by various routes including oral, nasal, topical, buccal and sublingual.

Formulations for oral administration may be in the form of capsules containing the active compounds dispersed in a binder such as gelatin or hydroxypropylmethyl cellulose, together with one or more of a lubricant, preservative, surface-active or dispersing agent. Such capsules or tablets may contain a controlled-release formulation as may be provided in a disposition of active compounds in hydroxypropylmethyl cellulose.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A therapeutic method for treating Alzheimer's Disease in an individual when such therapy is indicated, comprising administering to the individual a therapeutically effective amount of D-cycloserine and a therapeutically-effective amount of D-alanine, said D-cycloserine and said D-alanine being in a therapeutically-effective ratio, said therapeutically-effective ratio being in a range of about 1-to-1 to about 100-to-1 of said D-alanine to said D-cycloserine, said D-cycloserine being administered in an amount in a range from 1 mg to about 100 mg of D-cycloserine per unit dosage form.

2. The method of claim 1 wherein said D-cycloserine is administered in an amount in a range from about 2 mg to about 50 mg of D-cycloserine per unit dosage form.

3. The method of claim 2 wherein said D-cycloserine is administered in an amount in a range from about 2 mg to about 50 mg of D-cycloserine per unit dosage form.

4. A therapeutic method for treating age-associated memory impairment in an individual when such therapy is indicated, comprising administering to the individual a therapeutically effective amount of D-cycloserine and a therapeutically-effective amount of D-alanine, said D-cycloserine and said D-alanine being in a therapeutically-effective ratio, said therapeutically-effective ratio being in a range of about 1-to1 to about 100to1 of said D-alanine to said D-cycloserine, said D-cycloserine being administered in an amount in a range from 1 mg to about 100 mg of D-cycloserine per unit dosage form.

5. The method of claim 4 wherein said D-cycloserine is administered in an amount in a range from about 2 mg to about 50 mg of D-cycloserine per unit dosage form.

6. The method of claim 5 wherein said D-cycloserine is administered in an amount in a range from about 2 mg to about 50 mg of D-cycloserine per unit dosage form.

7. A therapeutic method for treating learning deficit in an individual when such therapy is indicated, comprising administering to the individual a therapeutically effective amount of D-cycloserine and a therapeutically-effective amount of D-alanine, said D-cycloserine and said D-alanine being in a therapeutically-effective ratio, said therapeutically-effective ratio being in a range of about 1-to1 to about 100-to-1 of said D-alanine to said D-cycloserine, said D-cycloserine being administered in an amount in a range from 1 mg to about 100 mg of D-cycloserine per unit dosage form.

8. The method of claim 7 wherein said D-cycloserine is administered in an amount in a range from about 2 mg to about 50 mg of D-cycloserine per unit dosage form.

9. The method of claim 8 wherein said D-cycloserine is administered in an amount in a range from about 2 mg to about 50 mg of D-cycloserine per unit dosage form.

10. A therapeutic method for improving memory or learning ability in a healthy individual, comprising administering to the individual a therapeutically effective amount of D-cycloserine and a therapeutically-effective amount of D-alanine, said D-cycloserine and said D-alanine being in a therapeutically-effective ratio, said therapeutically-effective ratio being in a range of about 1-to-1 to about 100-to-1 of said D-alanine to said D-cycloserine, said D-cycloserine being administered in an amount in a range from 1 mg to about 100 mg of D-cycloserine per unit dosage form.

11. The method of claim 10 wherein said D-cycloserine is administered in an amount in a range from about 2 mg to about 50 mg of D-cycloserine per unit dosage form.

12. The method of claim 11 wherein said D-cycloserine is administered in an amount in a range from about 2 mg to about 50 mg of D-cycloserine per unit dosage form.

13. A therapeutic method for treating a psychotic disorder in an individual when such therapy is indicated, comprising administering to the individual a therapeutically effective amount of D-cycloserine and a therapeutically-effective amount of D-alanine, said D-cycloserine and said D-alanine being in a therapeutically-effective ratio, said therapeutically-effective ratio being in a range of about 1-to-1 to about 100-to-1 of said D-alanine to said D-cycloserine, said D-cycloserine being administered in an amount in a range from 1 mg to about 100 mg of D-cycloserine per unit dosage form.

14. The method of claim 13 wherein said D-cycloserine is administered in an amount in range from about 2 mg to about 50 mg of D-cycloserine per unit dosage form.

15. The method of claim 14 wherein said D-cycloserine is administered in an amount in a range from about 2 mg to about 50 mg of D-cycloserine per unit dosage form.

16. The method of claim 13 wherein said psychotic disorder is a schizophrenic disorder.

17. The method of claim 16 wherein said schizophrenic disorder is a PCP-induced schizophrenic disorder.

* * * * *